United States Patent
Ziegler et al.

(10) Patent No.: US 11,980,922 B2
(45) Date of Patent: May 14, 2024

(54) METHODS FOR PRODUCING METAL MATRIX COMPOSITE STRIP PRODUCT

(71) Applicant: MATERION CORPORATION, Mayfield Heights, OH (US)

(72) Inventors: Karl R. Ziegler, Mayfield Heights, OH (US); Fritz Grensing, Mayfield Heights, OH (US); Jeffrey R. Campbell, Mayfield Heights, OH (US); Todd S. Osborn, Mayfield Heights, OH (US); Thomas F. Sirgey, Mayfield Heights, OH (US)

(73) Assignee: Materion Corporation, Mayfield Heights, OH (US)

( * ) Notice: Subject to any disclaimer, the term of this patent is extended or adjusted under 35 U.S.C. 154(b) by 769 days.

(21) Appl. No.: 17/271,533

(22) PCT Filed: May 6, 2019

(86) PCT No.: PCT/US2019/030850
§ 371 (c)(1),
(2) Date: Feb. 25, 2021

(87) PCT Pub. No.: WO2019/217278
PCT Pub. Date: Nov. 14, 2019

(65) Prior Publication Data
US 2021/0252571 A1    Aug. 19, 2021

Related U.S. Application Data

(60) Provisional application No. 62/668,434, filed on May 8, 2018.

(51) Int. Cl.
*B21B 3/00*    (2006.01)

(52) U.S. Cl.
CPC ............ *B21B 3/00* (2013.01); *B21B 2261/20* (2013.01); *B21B 2265/12* (2013.01)

(58) Field of Classification Search
CPC .......... B21B 3/00–02; B21B 2003/001; B21B 2261/20; B21B 2265/12; B21B 2001/225; B21B 1/26
See application file for complete search history.

(56) References Cited

U.S. PATENT DOCUMENTS

| | | | |
|---|---|---|---|
| 5,195,344 A | 3/1993 | Masuda et al. | |
| 5,384,087 A * | 1/1995 | Scorey | C22C 32/0063 419/57 |

(Continued)

FOREIGN PATENT DOCUMENTS

| | | |
|---|---|---|
| CN | 106424196 A | 2/2017 |
| JP | S63-220901 A | 9/1988 |

(Continued)

OTHER PUBLICATIONS

International Application No. PCT/US2019/030850, International Search Report dated Aug. 2, 2019, 2 pages.

(Continued)

*Primary Examiner* — Bobby Yeonjin Kim
(74) *Attorney, Agent, or Firm* — COZEN O'CONNOR

(57) ABSTRACT

Methods for producing a coiled strip of metal matrix composite (MMC) material are disclosed. The methods include a combination of hot rolling and warm rolling processes that reduce the thickness of the input material and increase its ductility. The resulting MMC strip can be coiled, which is useful for high volume coil-to-coil applications.

14 Claims, 6 Drawing Sheets

(56) References Cited

U.S. PATENT DOCUMENTS

| | | | | |
|---|---|---|---|---|
| 5,799,238 A | * | 8/1998 | Fisher, II | B22F 3/16 |
| | | | | 419/48 |
| 6,033,622 A | * | 3/2000 | Maruyama | B22F 1/18 |
| | | | | 427/217 |
| 2016/0273080 A1 | * | 9/2016 | Tarrant | C22C 1/1084 |
| 2018/0272428 A1 | * | 9/2018 | Plotnikov | C22C 47/14 |

FOREIGN PATENT DOCUMENTS

| | | |
|---|---|---|
| JP | 2001-252703 A | 9/2001 |
| JP | 2010-043335 A | 2/2010 |
| JP | 2011-500958 A | 1/2011 |
| JP | 2018-040034 A | 3/2018 |

OTHER PUBLICATIONS

Zahid, et al., "Superplasticity in an alulllinium alloy 2124/SiCp composite" Materials Science and Technology, vol. 14, No. 9-10, Dec. 31, 1998, pp. 901-905.

\* cited by examiner

METHODS FOR PRODUCING METAL MATRIX COMPOSITE STRIP PRODUCT

CROSS-REFERENCE TO RELATED APPLICATIONS

This application claims priority to U.S. Provisional Patent Application Ser. No. 62/668,434, filed May 8, 2018, the entirety of which is incorporated by reference herein.

BACKGROUND

The present disclosure relates to processing methods for metal matrix composites (MMC). In particular, the process allows for an MMC material to be produced as a strip that can be coiled. The process finds particular use with aluminum-silicon carbide (Al—SiC) metal matrix composites. This material includes silicon carbide particles dispersed in a matrix of an aluminum alloy. Also disclosed are coils of MMC materials and methods for producing such coils, articles formed from such a coilable strip material, and methods for making such articles.

Metal matrix composite (MMC) materials exhibit exceptional stiffness, high strength, high fatigue strength, high tensile strength at elevated temperatures, and wear resistance. However, these materials also have limited ductility and thus articles made from such materials are primarily produced by batch processes. It would be desirable to be able to provide MMC materials in forms that permit high volume processing using automated processing equipment.

BRIEF DESCRIPTION

The present disclosure relates to methods for processing metal matrix composites (MMC) such that the MMC material can be coiled into a strip. This processing decreases the strength of the MMC, but increases its ductility to prevent the creation of cracks that limit the ability to economically produce the thin gauge coilable strip.

Disclosed herein in various embodiments are methods for producing a strip of a metal matrix composite (MMC) material, comprising: hot working a rectangular input of the MMC material to produce a hot rolled MMC material; and warm working the hot rolled MMC material to obtain the strip of MMC material.

The strip of MMC material can subsequently be wound into a coil.

In some embodiments, the hot working is performed at a temperature above the MMC material's recrystallization temperature. In other embodiments, the hot working may be performed at a temperature of about 900° F. (482° C.) or higher. The hot working may be performed to a total % HW of at least 75%. The hot working may be performed by a plurality of hot passes, each hot pass resulting in a % HW of up to 20%.

The warm working may be performed at a temperature greater than room temperature and less than the recrystallization temperature of the MMC material. In particular embodiments, the warm working may be performed at a temperature from about 350° F. to about 600° F. (about 177° C. to about 315° C.). The warm working can be performed using heated rolls. The warm working can be performed to a total % WW of at least 75%. The warm working may be performed by a plurality of warm passes, each warm pass resulting in a % WW of up to 65%.

In further embodiments, the strip of MMC material is also cold worked after the warm working. The cold working may be performed to a total % CW of about 10% or less.

The MMC material comprises an aluminum alloy and ceramic particles dispersed in the aluminum alloy. The ceramic particles may comprise at least one ceramic material selected from the group consisting of carbides, oxides, silicides, borides, and nitrides, and in particular embodiments is silicon carbide. The MMC material may comprise from about 15 vol % to about 50 vol % of the ceramic particles. The average particle size of the ceramic particles may be from about 0.3 μm to about 5 μm.

In particular embodiments, the MMC material is a 6061 or 2124 aluminum alloy reinforced with about 15 vol % to about 50 vol % of silicon carbide. In other embodiments, the MMC material is a 6061, 6063, 6082, 2009, 2618 or 2124 aluminum alloy reinforced with about 10 vol % to about 50 vol % of silicon carbide. It should be appreciated that other ceramic particles may also be used instead of or in addition to silicon carbide.

Also disclosed herein are coiled strips of a metal matrix composite (MMC) material made according to the methods described above. Also disclosed are articles made from an un-coiled strip of a metal matrix composite (MMC) material.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
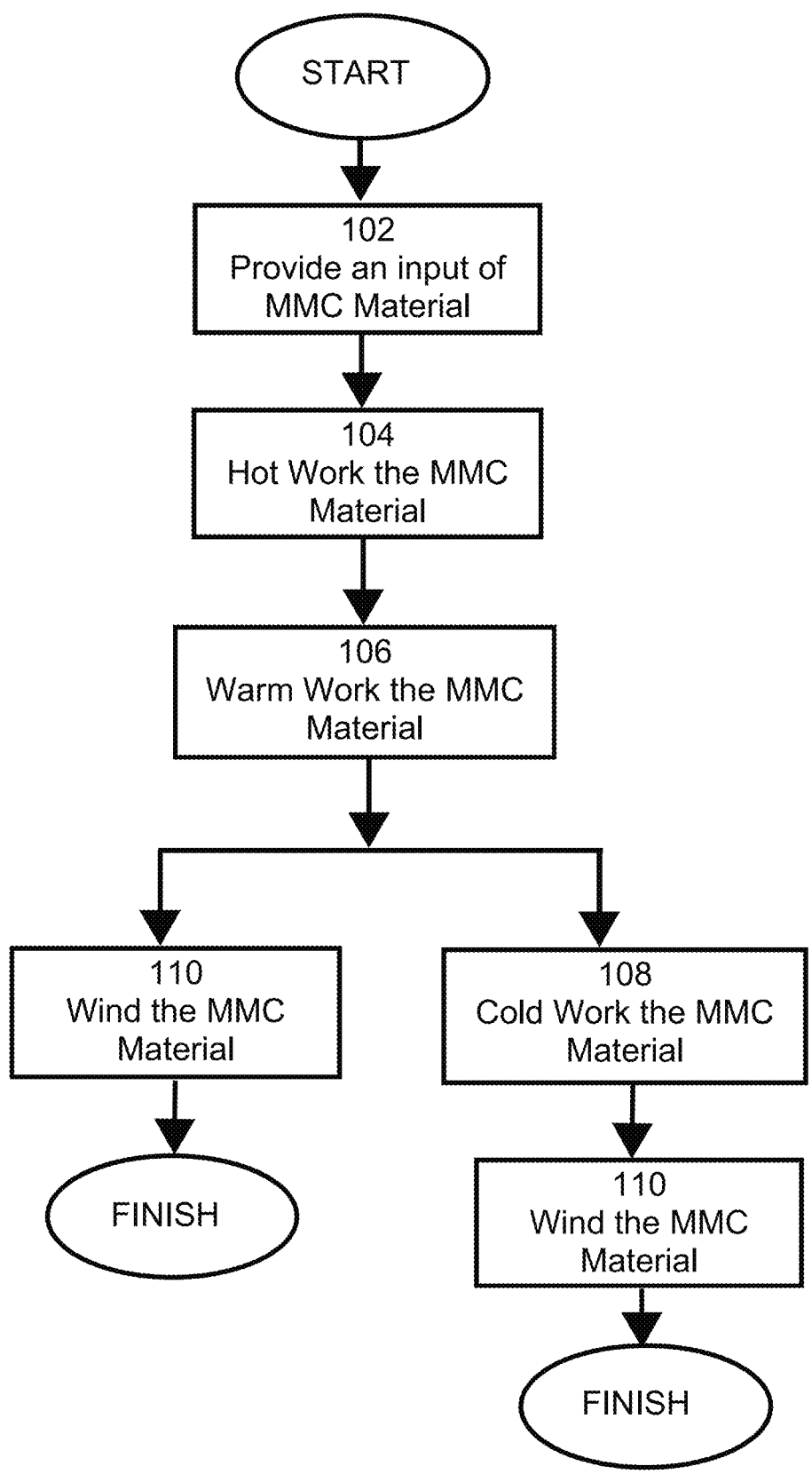
FIG. 1 is a diagram illustrating an exemplary process in accordance with some embodiments of the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/components/steps and permit the presence of other ingredients/components/steps. However, such description should be construed as also describing compositions, articles, or processes as "consisting of" and "consisting essentially of" the enumerated ingredients/components/steps, which allows the presence of only the named ingredients/components/steps, along with any impurities that might result therefrom, and excludes other ingredients/components/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams or 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

The present disclosure relates to materials having an average particle size. The average particle size is defined as the particle diameter at which a cumulative percentage of 50% (by volume) of the total number of particles are attained. In other words, 50% of the particles have a diameter above the average particle size, and 50% of the particles have a diameter below the average particle size. The size distribution of the particles will be Gaussian, with upper and lower quartiles at 25% and 75% of the stated average particle size, and all particles being less than 150% of the stated average particle size.

The present disclosure may refer to temperatures for certain process steps. In the present disclosure, the temperature usually refers to the temperature attained by the material that is referenced, rather than the temperature at which the heat source (e.g. furnace, oven) is set. The term "room temperature" refers to a range of from 68° F. (20° C.) to 77° F. (25° C.).

The term "bar" refers to a piece of material with a rectangular cross-section having a thickness of greater than 0.48 mm. The term "plate" refers to a piece of material with a rectangular cross-section having a thickness greater than 4.78 mm. The term "strip" refers to a piece of material with a rectangular cross-section having a thickness of 4.78 mm or less. The term "slab" refers to a piece of material that has a rectangular cross-section, and may be used interchangeably with the word "input" to refer to the starting piece of material that is worked by the processes of the present disclosure into a strip that can be coiled.

The term "coil" refers to a length of material that is wound into coil form, and may also be called a roll of material.

Rolling, as used herein, is a metal forming process in which a stock input is passed through one or more pairs of rollers to reduce the thickness of the stock input.

Metal matrix composite (MMC) materials are usually offered as discrete strips or plates for final product processing. This is primarily due to the limited ductility of MMC materials. As a result, batch processing methods must typically be used to produce the final product, which limits the cost-effectiveness of the MMC materials. It would be desirable to be able to process high volumes of material using automated coil-to-coil processing equipment. Thus, producing a coiled form of MMC material would be advantageous.

Cold working of MMC material results in cracks. The cracks are due to the relatively low ductility at room temperature of MMC material. The processes of the present disclosure avoid cracks, thus permitting a coiled MMC strip to be produced. The coil of MMC strip is useful for high volume coil-to-coil applications. This also enables cost-effective storage/transportation of the material as well as the production of articles therefrom.

A metal matrix composite is a composite material that includes a metal matrix and reinforcement particles dispersed in the metal matrix. The metal matrix phase is typically continuous, whereas the reinforcing particles form a dispersed phase within the metal matrix phase.

In the MMCs of the present disclosure, the matrix phase is formed from aluminum or an aluminum alloy. The reinforcement particles are a ceramic material selected from carbides, oxides, silicides, borides, and nitrides. Specific reinforcement particles include silicon carbide, titanium carbide, boron carbide, silicon nitride, titanium nitride, and zirconium oxide. In particular embodiments, silicon carbide is used.

The reinforcement particles may have an average particle size (D50) in the range of from 0.3 micrometers ($\mu$m) to 5 $\mu$m, including about 3 $\mu$m. The average particle size is defined as the particle diameter at which a cumulative percentage of 50% by volume (vol %) of the total volume of particles are attained. In other words, 50 vol % of the particles have a diameter above the average particle size, and 50 vol % of the particles have a diameter below the average particle size.

The MMC may include from about 10 vol % to about 50 vol % of the reinforcement particles, including from about 15 vol % to about 30 vol % and from about 30 vol % to about 50 vol %.

The aluminum alloy used in the MMC may be a 2000 series aluminum alloy (i.e., aluminum alloyed with copper), a 6000 series aluminum alloy (i.e., aluminum alloyed with magnesium and silicon), or a 7000 series aluminum alloy (i.e., aluminum alloyed with zinc). Non-limiting examples of suitable aluminum alloys include 2009, 2124, 2090, 2099, 6061, and 6082.

In some embodiments, the aluminum alloy includes from about 91.2 wt % to about 94.7 wt % aluminum, from about 3.8 wt % to about 4.9 wt % copper, from about 1.2 wt % to about 1.8 wt % magnesium, and from about 0.3 wt % to about 0.9 wt % manganese.

In other embodiments, the aluminum alloy includes from about 95.8 wt % to about 98.6 wt % aluminum, from about 0.8 wt % to about 1.2 wt % magnesium, and from about 0.4 wt % to about 0.8 wt % silicon.

In some particular embodiments, an MMC includes 6061 series or 2124 series aluminum alloy reinforced with about 10 vol % to about 50 vol % of silicon carbide particles, including from about 15 vol % to about 30 vol % and from about 30 vol % to about 50 vol % of silicon carbide particles.

In more particular embodiments, the MMC material can be made from a 6061 aluminum alloy reinforced with 40 vol % silicon carbide particles. Physical properties of 6061 aluminum alloy reinforced with 40 vol % silicon carbide particles include:

| Physical Properties | |
|---|---|
| Density, g/cm$^3$ (lbs/in$^3$) | 2.9 (0.105) |
| Elastic Modulus, GPa (msi) | 140 (20.3) |
| Specific Stiffness, GPa/g/cm$^3$ | 48 |
| Poisson's Ratio | 0.3 |
| Thermal Conductivity @ 25° C. W/m° K (BTU/hr · ft. ° F.) | 130 (75) |
| Thermal Expansion @ 25° C. ppm/° C. (ppm/° F.) | 13 (7.4) |
| Solidus ° C. (° F.) | 570 (1058) |
| Specific Heat Capacity J/g/° C. (BTU/lb/° F.) | 0.800 (0.191) |

In other particular embodiments, the MMC material can be made from a 6061 aluminum alloy reinforced with 20 vol % silicon carbide particles. Physical properties of 6061 aluminum alloy reinforced with 20 vol % silicon carbide particles include:

| Physical Properties | |
|---|---|
| Density, g/cm$^3$ (lbs/in$^3$) | 2.8 (0.101) |
| Elastic Modulus, GPa (msi) | 103 (14.9) |
| Specific Stiffness, GPa/g/cm$^3$ | 36 |
| Poisson's Ratio | 0.3 |
| Thermal Conductivity @ 25° C. W/m° K (BTU/hr · ft. ° F.) | 150 (87) |
| Thermal Expansion @ 25° C. ppm/° C. (ppm/° F.) | 17 (9.4) |
| Solidus ° C. (° F.) | 570 (1058) |
| Specific Heat Capacity J/g/° C. (BTU/lb/° F.) | 0.850 (0.203) |

In additional embodiments, the MMC material can be made from a 2124 aluminum alloy reinforced with 25 vol % silicon carbide particles. Physical properties of 2124 aluminum alloy reinforced with 25 vol % silicon carbide particles include:

| Physical Properties | |
|---|---|
| Density, g/cm$^3$ (lbs/in$^3$) | 2.88 (0.104) |
| Elastic Modulus, GPa (msi) | 115 (16.7) |
| Specific Stiffness, GPa/g/cm$^3$ | 39 |
| Poisson's Ratio | 0.3 |
| Thermal Conductivity @ 25° C. W/m° K (BTU/hr · ft. ° F.) | 150 (87) |
| Thermal Expansion @ 25° C. ppm/° C. (ppm/° F.) | 16.1 (8.9) |
| Solidus ° C. (° F.) | 548 (1018) |
| Specific Heat Capacity J/g/° C. (BTU/lb/° F.) | 0.836 (0.200) |

In particular embodiments, the MMC material can be made from 2124 aluminum alloy reinforced with 17 vol % silicon carbide particles. Physical properties of 2124 aluminum alloy reinforced with 17 vol % silicon carbide particles include:

| Physical Properties | |
|---|---|
| Density, g/cm$^3$ (lbs/in$^3$) | 2.85 (0.103) |
| Elastic Modulus, GPa (msi) | 100 (14.5) |
| Specific Stiffness, GPa/g/cm$^3$ | 35 |
| Poisson's Ratio | 0.3 |
| Thermal Conductivity @ 25° C. W/m° K (BTU/hr · ft. ° F.) | 155 (90) |
| Thermal Expansion @ 25° C. ppm/° C. (ppm/° F.) | 16.8 (9.3) |
| Solidus ° C. (° F.) | 548 (1018) |
| Specific Heat Capacity J/g/° C. (BTU/lb/° F.) | 0.848 (0.203) |

In other embodiments, the MMC material can be made from 6063, 6082, 2009, or 2618 series aluminum alloys reinforced with about 10 vol % to about 50 vol % of silicon carbide particles, including from about 15 vol % to about 30 vol %, or from about 30 vol % to about 50 vol % of silicon carbide particles.

In some particular embodiments, the MMC material is made of 2009 series aluminum alloy reinforced with 15 vol % silicon carbide particles. Physical properties of 2009 series aluminum alloy reinforced with 15 vol % silicon carbide particles include:

| Physical Properties | |
|---|---|
| Density, g/cm$^3$ (lbs/in$^3$) | 2.86 (0.103) |
| Elastic Modulus, GPa (msi) | 96 (13.9) |
| Specific Stiffness, GPa/g/cm$^3$ | 33 |
| Poisson's Ratio | 0.3 |
| Thermal Conductivity @ 25° C. W/m° K (BTU/hr · ft. ° F.) | 155 (90) |
| Thermal Expansion @ 25° C. ppm/° C. (ppm/° F.) | 18 (10.0) |
| Solidus ° C. (° F.) | 548 (1018) |
| Specific Heat Capacity J/g/° C. (BTU/lb/° F.) | 0.848 (0.203) |

Generally, the manufacture of the input MMC materials can be done by any suitable method, such as powder metal production (including, but not limited to, powder metallurgy and high energy mixing processes discussed above). The MMC materials of the present disclosure are made by mixing the aluminum alloy with reinforcement particles to form a mixture. The mixture is consolidated, compacted and extruded or hot rolled. This process creates a rectangular product, i.e. a slab, which is used as the input into the processes of the present disclosure to produce a coiled MMC strip.

For example, metal powder and ceramic particles may be mixed with a high energy technique to distribute the ceramic reinforcement particles into the metal matrix. Suitable techniques for this mixing include ball milling, mechanical attritors, teamer mills, rotary mills and other methods to provide high energy mixing to the powder constituents. Mechanical alloying should be completed in an atmosphere to avoid excessive oxidation of powders. For example, an inert atmosphere can be provided using nitrogen or argon gas. The processing parameters should be selected to achieve an even distribution of the ceramic particles in the metallic matrix.

The powder from the high energy mixing stage may be degassed to remove any retained moisture from the powder surface. This may be completed at between 37° C. and 500° C. (100° F. to 930° F.).

A hot compacting step may also be performed to increase a density of the reinforced composite structure. The hot compacting steps may be performed at a temperature in the range of from about 750° F. (400° C.) to about 1112° F. (600° C.), including from about 795° F. (425° C.) to about 1020° F. (550° C.) and about 930° F. (500° C.). Hot compaction may include the use of hot die compaction, hot isostatic pressing or hot extrusion typically at pressures of between 30 to 150 MPa.

The mixture is consolidated by hot isostatic pressing (HIP). In the HIP process, the powder is exposed to both elevated temperature and high gas pressure in a high pressure containment vessel to turn the powder into a compact solid. The isostatic pressure is omnidirectional. The HIP process eliminates voids and pores. The hot isostatic pressing may be performed at a temperature of 660° F. (350° C.) to 1110° F. (600° C.) and a pressure of 30 to 150 MPa for a period of sufficient to allow the metal section to reach the required temperature, typically between 1 hour and 8 hours. The hot isostatic pressing may be performed on commercially available aluminum alloy, steel, or nickel HIP systems.

The present disclosure relates to methods or processes for processing an input of MMC material having a rectangular shape into a coiled strip. Generally, the input can have any thickness, and for example can be a plate or a strip. The input material can have any length, for example several feet to hundreds of feet long. The processing method works the MMC material at a combination of elevated and room temperatures to produce a strip of MMC material that can be coiled. The methods disclosed herein use combinations of hot working; warm working; and cold working conditions to economically produce a coiled strip product.

Generally, MMCs, such as the above disclosed Al—SiC MMCs, exhibit limited ductility at room temperature. In other words, the MMC material has a limited ability to deform under pressure or compressive stress, such as the stresses which are applied to the input material during rolling. Processing these materials via conventional methods to produce coiled strip results in cracking of the material. This severely limits the ability to economically produce thin gauge MMC strip. The cracks are caused by the lower ductility of the MMC materials at room temperatures as well as the build-up of cold work in the material.

The ductility of an MMC material can be improved by elevating the temperature of the material during the rolling processes of the present disclosure. Several things happen to the material when the temperature is increased. First, the strength of the material is decreased, allowing for more reduction per a given load of material in the rolling process. Second, the ductility of the aluminum matrix of the MMC material increases with temperature. At temperatures around about 350° F. (175° C.) to about 600° F. (315° C.), the aluminum alloy microstructure in Al—SiC MMC material recovers from rolling induced deformation. This allows one to achieve much larger total deformations than are possible at lower temperatures.

FIG. 1 is a flowchart showing the process steps in an exemplary embodiment of a process 100 to produce a coiled strip from a rectangularly shaped MMC input material. In a first step 102, a rectangularly shaped slab of MMC material is provided for input into rolling equipment, such a rolling mill. The input material may be a strip or a plate, for example, and have a relatively large thickness.

In some embodiments, the input material is provided continuously, e.g. via a continuous casting process. In these continuous processes, molten material is solidified into the rectangular input shape for subsequent rolling in a rolling mill. In other embodiments, the input material may include discrete pieces of rectangular input material suitable for rolling in batch processes.

The MMC input material undergoes a first hot working step 104. Hot working is a metal forming process in which an alloy is passed through rolls, dies, or is forged to reduce the section of the alloy and to make the desired shape and dimension, at a temperature generally above the recrystallization temperature of the alloy. This generally reduces directionality in mechanical properties, and produces a new equiaxed microstructure. The degree of hot working performed is indicated in terms of % reduction in thickness, or % HW. The hot working is usually performed by hot rolling.

Rolling is a metal forming process in which the input is passed through one or more pairs of rollers to reduce the thickness of the input and make the thickness of the input uniform. In hot rolling, the temperature of the metal is raised above its recrystallization temperature. The hot rolling step is carried out at a temperature from about 900° F. (480° C.) to about 1050° F. (565° C.) r, i.e. the input is heated to this temperature before being passed through the rolling mill. The input material is relatively thick, and thus maintains the needed temperature during the hot rolling process. In some embodiments, the input material is already in a heated state, e.g. taken directly from a continuous casting process. In other embodiments, the MMC input material is heated from a temperature lower than the desired hot processing temperature to the desired hot working temperature.

It is contemplated that the input material is not canned while being heated or hot worked. Canning refers to placing the input material between two sheets of metal and then welding/sealing the two sheets to encapsulate the input material. Canning isolates the input material from the potentially oxygen rich and contaminant containing ambient atmosphere or environment. Thus, corrosion and oxidation of the material is reduced when the material is canned while being heated as oxidation occurs more rapidly at molten metal temperatures. Canning is generally useful only when the input material is less than about 4 feet long, and this will not occur in contemplated commercial manufacturing processes.

The reduction in thickness (% HW) of the input material in the hot working process 104 may vary. Generally, MMCs of the present disclosure may be hot rolled with up to 30% reduction in thickness per rolling pass. In some embodiments, the thickness reduction per pass is from about 5% to about 30%. In other embodiments, the thickness reduction per pass is from about 10% to about 30%. In some embodiments, the hot rolling thickness reduction per pass may be from about 10% to about 25%. The input material may experience more than one rolling pass. In some embodiments, the input material may be passed through mill rolls 2, 3, 4, 5, 6 7, 8, 9, or 10 times.

The maximum total reduction (% HW) in the hot working step, i.e. after all hot rolling passes are completed, is about 75% of the input thickness of the MMC material, although more than 75% reduction is acceptable. When the workpiece becomes too thin, it loses heat too quickly for hot working to occur. In some embodiments, no intermediate re-heating of the input material is needed between rolling passes. In other embodiments, the material may be reheated between rolling passes.

After the hot working step, the hot worked MMC material undergoes a warm working process 106. This is generally performed by warm rolling. The warm rolling step is carried out with the hot worked MMC material still at an elevated temperature. Desirably, the MMC material is at a temperature of about 350° F. to about 600° F. (about 175° C. to about 315° C.). In some embodiments, the rollers used for the warm rolling are also heated to this temperature. In other words, the rollers are heated such that they conduct heat to the MMC material. Generally, MMCs are good conductors of heat, and the MMC material is thin enough after the hot working that the heat can penetrate the entire thickness of the MMC material.

In some embodiments, at least one roll of a rolling mill employed in the warm working step is heated. The rolls may be heated to match the temperature range preferred for warm rolling. The rolls may be heated by various methods known in the art, for example by having a resistance heating element inserted into the rolls.

The reduction of the thickness (% WW) of the MMC material in the warm working process 106 may be up to 65% per rolling pass. In other embodiments, the reduction per pass is from about 5% to about 65%. In some embodiments, the warm working reduction may be from about 10% to about 30%. In some embodiments, the warm working reduction may be from about 10% to about 25%. In some embodiments, the warm working process includes multiple passes through the rolling mill. In some embodiments, the input MMC material may be passed through a rolling mill 2, 3, 4, 5, 6 7, 8, 9, or 10 times.

The total reduction in thickness of the warm working step, i.e. after all warm rolling passes are completed, is at least 75% of the starting thickness (i.e. the thickness of the MMC material after the hot working has been performed). In some embodiments, the total reduction in thickness of the warm working step is about 90% of the starting thickness of the MMC material after the how working has been performed.

The warm rolling process 106 is advantageous because it eliminates or at least greatly reduces the presence of edge cracks in MMC material. Moreover, the warm rolling process allows larger reductions in the thickness of the MMC material per pass on the rolling mill compared to cold working. The relatively low rolling temperature, compared to hot rolling temperatures, limits the oxidation of the material, as the material is more susceptible to rapid oxidation at hot rolling temperatures.

In some embodiments, after the warm working process 106, the MMC material undergoes an optional cold working process 108. That is, the material from the warm working process is allowed to cool and then fed into a working mill. Cold working is the process of mechanically altering the shape or size of the metal by plastic deformation. This can be done by rolling, drawing, pressing, spinning, extruding or heading of the metal or alloy. When a metal is plastically deformed, dislocations of atoms occur within the material. Particularly, the dislocations occur across or within the grains of the metal. The dislocations over-lap each other and the dislocation density within the material increases. The increase in over-lapping dislocations makes the movement of further dislocations more difficult. This increases the hardness and tensile strength of the resulting alloy while generally reducing the ductility and impact characteristics of the alloy. Cold working also improves the surface finish of the alloy. Mechanical cold working is generally performed at a temperature below the recrystallization point of the alloy, and is usually done at room temperature. The percentage of cold working (% CW), or the degree of deformation, can be determined by measuring the change in the cross-sectional area of the alloy before and after cold working.

The cold working process 108 is carried out at about room temperature. The MMC material itself should be at room temperature. Due to the limited ductility of the MMC material, the total reduction in thickness (% CW) of the MMC material is limited to about 10% or less. In some embodiments, the cold working process includes multiple passes through the rolling mill. In some embodiments, the MMC material may be passed through the rolling mill 2, 3, 4, 5, 6 7, 8, 9, or 10 times.

Desirably, after these steps, the resulting MMC strip has a thickness of about 0.04 millimeter (mm) to about 1.25 mm.

Figure 2:
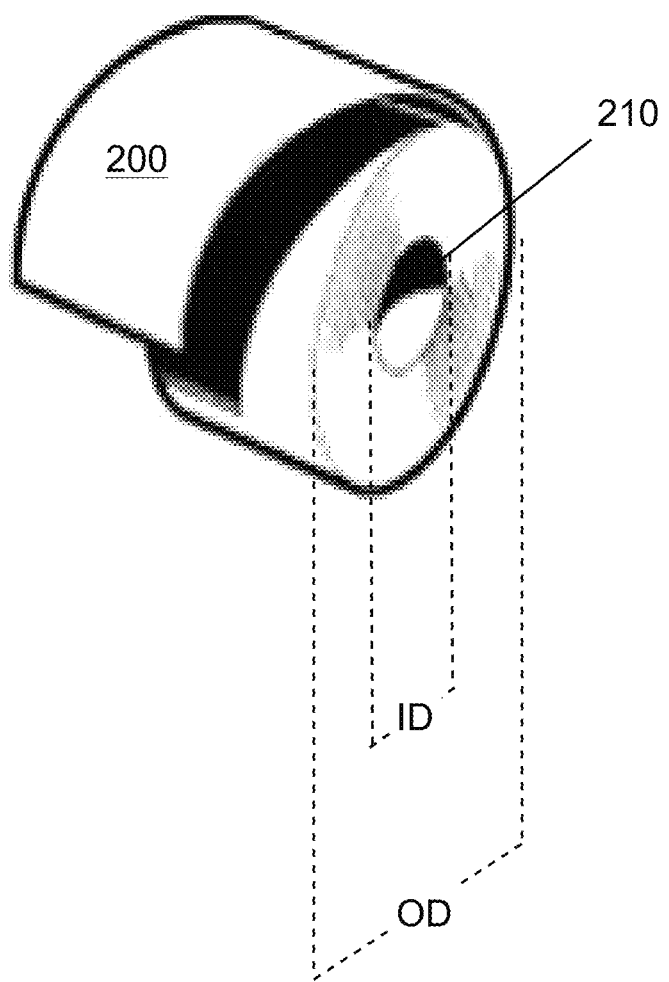
FIG. 2 is an illustration of a wound coil produced in accordance with some embodiments of the present disclosure.

In some embodiments, the process 100 further includes a winding step 110. That is, with reference to FIG. 2, the material may be wrapped about itself to create a larger roll or coil of material 200. In some embodiments, the material is wrapped about a core 210. In some embodiments, the coil form 200 has an inner diameter ID from about 16 inches to about 20 inches. In some embodiments, the coil form has an outer diameter OD from about 60 inches to about 72 inches. The core 210 also provides a means by which the material can be stored and transported.

The resulting MMC coiled strip material can be used for high volume production of MMC materials. The MMC material can be uncoiled and converted into an article that is useful in applications such as space, defense, aerospace, automotive, OEM, consumer goods, consumer electronics, and transportation applications. For example, the uncoiled MMC strip can be stamped, cut, etc. to form the article. Articles can include outlet guide vanes; hydraulic/fuel blocks; wheels; fixed wing structures/skins; helicopter components; pistons; piston pins; cylinder liners; brake calipers; connecting rods; push rods; chassis components; optical sensors; and satellite structures.

The following examples are provided to illustrate the compositions, articles, and methods of the present disclosure. The examples are merely illustrative and are not intended to limit the disclosure to the materials, conditions, or process parameters set forth therein.

EXAMPLES

Comparative Example 1

Figure 3A:
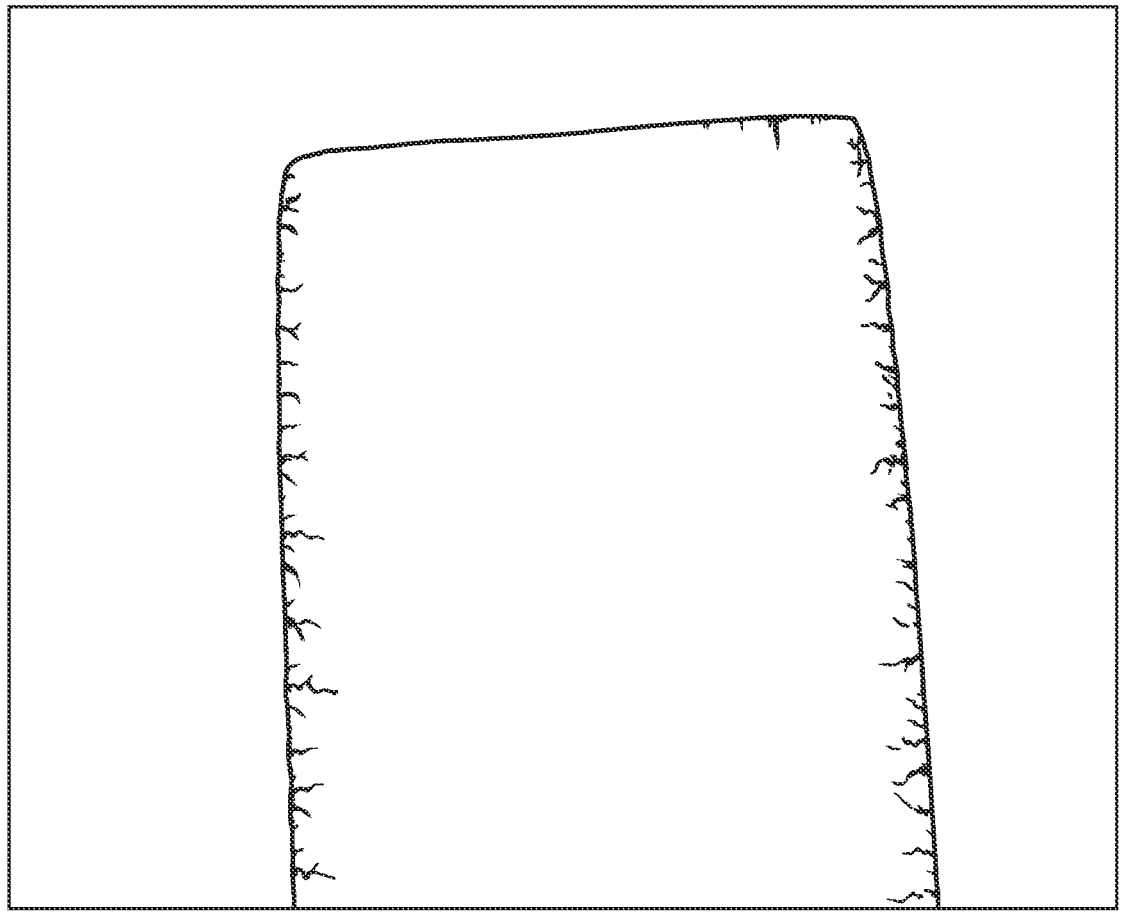
FIG. 3A and FIG. 3B are photographs of short strips of an MMC material that is only cold worked, and both strips exhibit cracking.
Figure 3B:
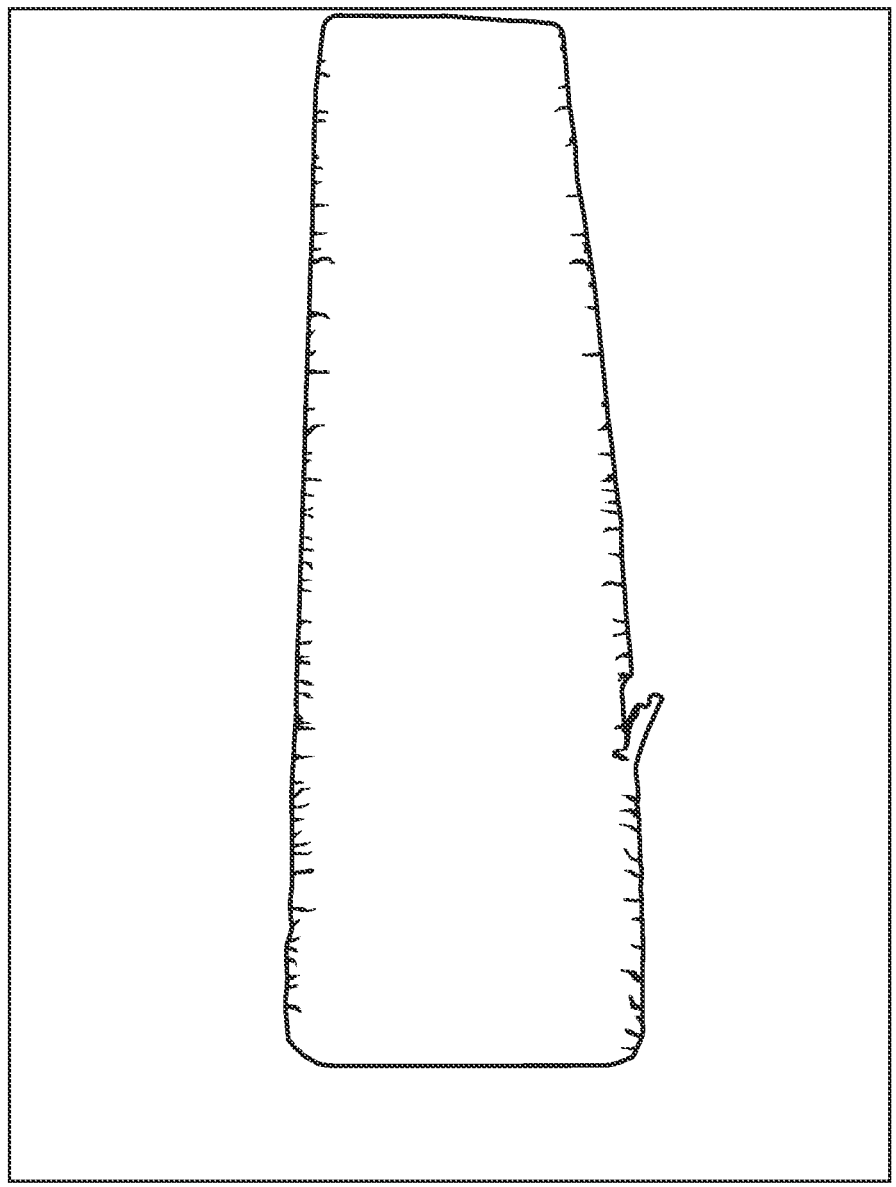

Pieces of an MMC made from 6061 aluminum alloy reinforced with 20 vol % of SiC particles were extruded at a thickness of 0.140 inches (3.55 mm), and cut to a width of 4.75 inches. The pieces were cold rolled at 10% CW per pass. As seen in FIG. 3A and FIG. 3B, edge cracking occurred.

Example 1

Figure 4:
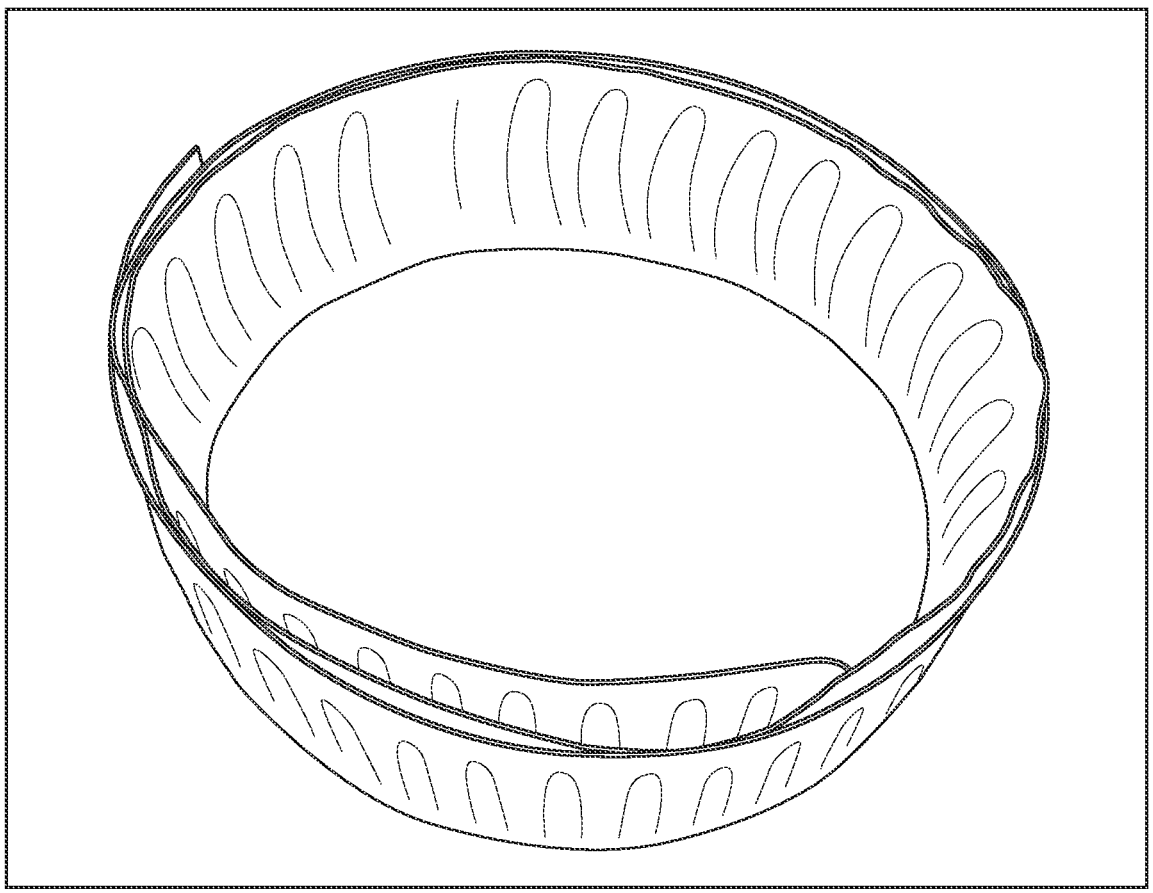
FIG. 4 is a photograph of a strip material processed in accordance with some embodiments of the present disclosure, and having enhanced properties.

Pieces of an MMC made from 6061 aluminum alloy reinforced with 20 vol % of SiC particles were extruded at a thickness of 0.140 inches (3.55 mm), and cut to a width of 4.75 inches. The pieces were warm rolled at temperatures from 450° F. to 550° F. (232° C. to 287° C.) to a thickness of 0.018 inch (0.46 mm), or a % WW of 87% thickness and a 4.75 inch width. As illustrated in FIG. 4, no cracks were present in the material, and the material was easily coiled.

Example 2

Pieces of an MMC made from 6061 aluminum alloy reinforced with 20 vol % of SiC particles were extruded at a thickness of 0.140 inches (3.55 mm) and a width of 4.5 inches. The edges were left as-extruded.

A Grieve furnace was used to preheat the samples. The furnace was set to 700° F. (370° C.), and the sample was held for 30 minutes in the furnace. A Fenn rolling mill was used to warm roll the MMC sample. The rolls were preheated to about 600° F. (315° C.) prior to rolling. A thermal glove was used to transfer the sample from the furnace to the rolling mill. The MMC sample was placed on the entry table of the rolling mill and the rolling sequence was immediately engaged. Temperature was measured by contact with a pyrometer on the tail of the piece at the start of the rolling process. After exiting the rolling mill, the sample was quickly transferred back to the entry side of the rolling mill. In the first sample, 7 passes were completed before the temperature dropped below 400° F. (204° C.). The data for each pass of the first sample (input length of 9 inches) is presented in Table 1, below.

Table 2 presents data for a second sample with a starting thickness of 0.140 inches and an input length of 9 inches. Table 3 presents data for a third sample with a starting thickness of 0.140 inches and an input length of 18 inches. Table 4 presents data for a fourth sample with a starting thickness of 0.140 inches and an input length of 36 inches. Table 5 presents data for a fifth sample with a starting thickness of 0.140 inches and an input length of 48 inches.

TABLE 1

| Input Thickness (in) | Output thickness (in) | Thickness change (in) | Reduction/ pass (%) | Temperature (tail) (° F.) |
|---|---|---|---|---|
| 0.140 | 0.139 | 0.001 | 0.7% | 500 |
| 0.139 | 0.131 | 0.008 | 5.8% | 430 |
| 0.131 | 0.123 | 0.008 | 6.1% | 460 |
| 0.123 | 0.110 | 0.013 | 10.6% | |
| 0.110 | 0.085 | 0.025 | 22.7% | 475 |
| 0.085 | 0.057 | 0.028 | 32.9% | 395 |
| 0.057 | 0.021 | 0.036 | 63.2% | |

TABLE 2

| Input Thickness (in) | Output Thickness (in) | Thickness Change (in) | Reduction/ pass (%) | Total Reduction (%) | Length (in) |
|---|---|---|---|---|---|
| 0.140 | 0.119 | 0.021 | 15.0% | 15.0% | 10.6 |
| 0.119 | 0.092 | 0.027 | 22.7% | 34.3% | 13.7 |
| 0.092 | 0.070 | 0.023 | 24.5% | 50.4% | 18.1 |
| 0.070 | 0.053 | 0.017 | 23.7% | 62.1% | 23.8 |
| 0.053 | 0.037 | 0.016 | 30.2% | 73.6% | 34.1 |
| 0.037 | 0.026 | 0.011 | 29.7% | 81.4% | 48.5 |
| 0.026 | 0.016 | 0.010 | 34.5% | 88.6% | 78.8 |
| 0.016 | 0.016 | 0.001 | 3.1% | 88.9% | 81.3 |

TABLE 3

| Input Thickness (in) | Output Thickness (in) | Thickness Change (in) | Reduction/ pass (%) | Total Reduction (%) | Length (in) |
|---|---|---|---|---|---|
| 0.140 | 0.117 | 0.023 | 16.4% | 16.4% | 21.5 |
| 0.117 | 0.095 | 0.022 | 18.8% | 32.1% | 26.5 |
| 0.095 | 0.081 | 0.014 | 14.7% | 42.1% | 31.1 |
| 0.081 | 0.635 | 0.018 | 21.6% | 54.6% | 39.7 |
| 0.064 | 0.050 | 0.013 | 20.5% | 63.9% | 49.9 |
| 0.051 | 0.040 | 0.011 | 20.8% | 71.4% | 63.0 |
| 0.040 | 0.029 | 0.011 | 27.5% | 49.3% | 86.9 |
| 0.029 | 0.025 | 0.004 | 13.8% | 82.1% | 100.8 |
| 0.025 | 0.018 | 0.007 | 28.8% | 87.1% | 140.0 |

TABLE 4

| Input Thickness (in) | Output Thickness (in) | Thickness Change (in) | Reduction/ pass (%) | Total Reduction (%) | Length (in) |
|---|---|---|---|---|---|
| 0.140 | 0.133 | 0.007 | 5.0% | 5.0% | 37.9 |
| 0.133 | 0.112 | 0.022 | 16.2% | 20.4% | 45.2 |
| 0.112 | 0.086 | 0.026 | 22.9% | 38.6% | 58.6 |
| 0.086 | 0.068 | 0.018 | 20.9% | 51.4% | 74.1 |
| 0.068 | 0.525 | 0.016 | 22.8% | 62.5% | 96.0 |
| 0.053 | 0.039 | 0.014 | 25.7% | 72.1% | 129.2 |
| 0.039 | 0.026 | 0.013 | 33.3% | 81.4% | 193.8 |

TABLE 4-continued

| Input Thickness (in) | Output Thickness (in) | Thickness Change (in) | Reduction/ pass (%) | Total Reduction (%) | Length (in) |
|---|---|---|---|---|---|
| 0.026 | 0.019 | 0.007 | 27.7% | 86.6% | 298.2 |
| 0.019 | 0.014 | 0.005 | 25.5% | 90.0% | |

TABLE 5

| Input Thickness (in) | Output Thickness (in) | Thickness Change (in) | Reduction/ pass (%) | Total Reduction (%) | Length (in) |
|---|---|---|---|---|---|
| 0.140 | 0.123 | 0.017 | 12.1% | 12.1% | 54.6 |
| 0.123 | 0.101 | 0.022 | 17.9% | 29.9% | 66.5 |
| 0.101 | 0.087 | 0.014 | 13.9% | 37.9% | 77.2 |
| 0.087 | 0.072 | 0.015 | 17.2% | 48.6% | 93.3 |
| 0.072 | 0.055 | 0.017 | 23.6% | 60.7% | 122.2 |
| 0.055 | 0.038 | 0.017 | 30.9% | 72.9% | 176.8 |
| 0.038 | 0.278 | 0.010 | 26.8% | 80.1% | 241.7 |
| 0.028 | 0.182 | 0.011 | 39.2% | 87.9% | 397.6 |

Example 3

Pieces of an MMC made from 6061 aluminum alloy reinforced with 20 vol % of SiC particles were made as in Example 2, but with a starting thickness of 0.057 inches (1.45 mm), and a starting length of 20.5 inches. The edges were left as-extruded. The sample was then rolled using warm rollers. The process was identical to that of Example 2. The results of each pass are presented below in Table 6. The ending strip had a length of 64.9 inches.

TABLE 6

| Input Thickness (in) | Output Thickness (in) | Thickness Change (in) | Reduction/ pass (%) | Total Reduction (%) | Temp (° F.) |
|---|---|---|---|---|---|
| 0.057 | 0.047 | 0.010 | 17.5% | 17.5% | 240 |
| 0.042 | 0.034 | 0.008 | 19.0% | 40.4% | |
| 0.027 | 0.027 | 0.000 | 0.0% | 52.6% | |
| 0.027 | 0.024 | 0.003 | 11.1% | 57.9% | 195 |
| 0.024 | 0.020 | 0.004 | 16.7% | 64.9% | |
| 0.020 | 0.018 | 0.002 | 10.0% | 68.4% | 140 |

Figure 5:
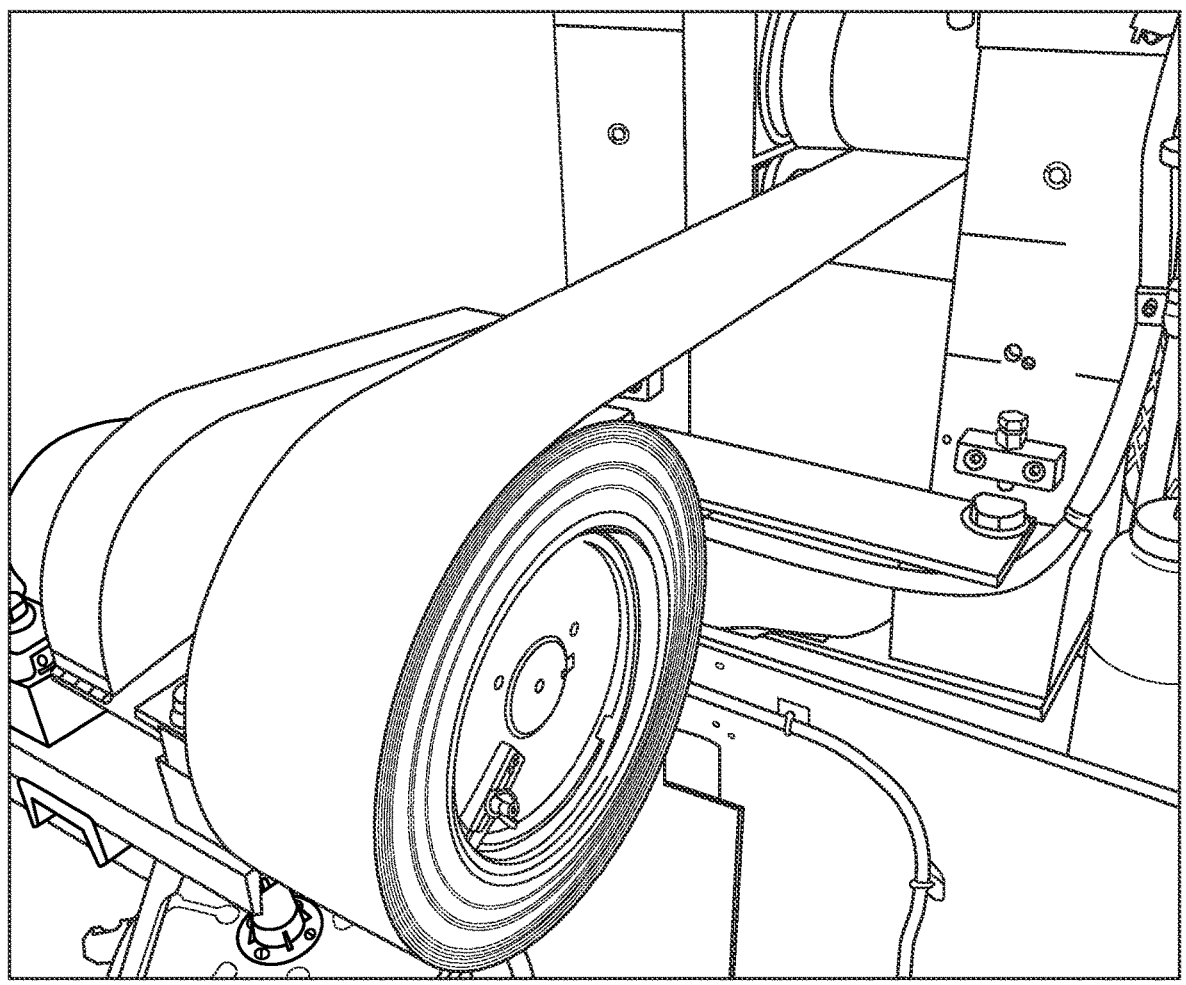
FIG. 5 is a photograph of coiled strip exiting the equipment used for warm rolling.

FIG. 5 is a picture of coiled MMC strip exiting a rolling mill used for warm rolling.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims or the equivalents thereof.

The invention claimed is:

1. A method for producing a strip of a metal matrix composite (MMC) material, comprising:
   hot working a rectangular input of the MMC material to produce a hot rolled MMC material; and
   warm working the hot rolled MMC material to obtain the strip of MMC material, wherein the warm working is performed using heated rolls.

2. The method of claim 1, further comprising winding the strip of MMC material into a coil.

3. The method of claim 1, wherein the hot working is performed at a temperature from about 900° F. (482° C.) to about 1050° F. (565° C.).

4. The method of claim 1, wherein the hot working is performed to a total % HW of at least 75%.

5. The method of claim 1, wherein the hot working is performed by a plurality of hot passes, each hot pass resulting in a % HW of up to 20%.

6. The method of claim 1, wherein the warm working is performed at a temperature from about 350° F. to about 600° F. (about 177° C. to about 315° C.).

7. The method of claim 1, wherein the warm working is performed to a total % WW of at least 75%.

8. The method of claim 1, wherein the warm working is performed by a plurality of warm passes, each warm pass resulting in a % WW of up to 65%.

9. The method of claim 1, further comprising cold working the strip of MMC material after the warm working.

10. The method of claim 9, wherein the cold working is performed to a total % CW of about 10% or less.

11. The method of claim 1, wherein the MMC material comprises an aluminum alloy and ceramic particles dispersed in the aluminum alloy.

12. The method of claim 11, wherein the ceramic particles comprise at least one ceramic material selected from the group consisting of carbides, oxides, silicides, borides, and nitrides.

13. The method of claim 1, wherein the MMC material comprises from about 15 vol % to about 50 vol % of the ceramic particles.

14. The method of claim 1, wherein the average particle size of the ceramic particles is from about 0.3 μm to about 0.5 μm.

* * * * *